United States Patent
Chiodo et al.

(10) Patent No.: US 7,506,543 B2
(45) Date of Patent: Mar. 24, 2009

(54) FOOT PRESSURE DETECTION DEVICE

(76) Inventors: Christopher P. Chiodo, 7 Bramel Cir., Walpole, MA (US) 02081; Brent G. Parks, 2731 Wynfield Rd., West Friendship, MD (US) 21794; Lew C. Schon, 2917 Old Court Rd., Baltimore, MD (US) 21208; Lynne Chiodo, 7 Bramel Cir., Walpole, MA (US) 02081

(*) Notice: Subject to any disclaimer, the term of this patent is extended or adjusted under 35 U.S.C. 154(b) by 139 days.

(21) Appl. No.: 11/359,444

(22) Filed: Feb. 23, 2006

(65) Prior Publication Data

US 2007/0161920 A1  Jul. 12, 2007

(51) Int. Cl.
*A61B 5/00* (2006.01)
(52) U.S. Cl. ........................................ 73/172
(58) Field of Classification Search ............... 73/172
See application file for complete search history.

(56) References Cited

U.S. PATENT DOCUMENTS

| | | | |
|---|---|---|---|
| 4,639,960 A * | 2/1987 | Quillen et al. | 5/710 |
| 4,740,475 A * | 4/1988 | Paul | 436/165 |
| 4,911,671 A * | 3/1990 | Rogers | 446/81 |
| 5,107,854 A * | 4/1992 | Knotts et al. | 600/592 |
| 5,484,318 A * | 1/1996 | Mayert et al. | 446/75 |
| 5,642,096 A * | 6/1997 | Leyerer et al. | 340/573.1 |
| 5,813,142 A * | 9/1998 | Demon | 36/29 |
| 6,721,980 B1 * | 4/2004 | Price et al. | 5/713 |

* cited by examiner

*Primary Examiner*—Max Noori
(74) *Attorney, Agent, or Firm*—Holland & Knight LLP; John P. Moran

(57) ABSTRACT

According to a first embodiment of our invention, a monitoring device is placed above, within, or on the bottom of a cast, boot, shoe, or other lower extremity immobilization or protective device, and has one or more single or cluster of pressure sensitive chambers designed to burst at a predetermined force or weight. The pressure sensitive chambers may be filled with air, liquid, semi-liquid, or particulate material. Once properly positioned, the device serves to detect and alert one or more individuals to the fact that weight-bearing has occurred and/or that a certain amount of force has been transmitted across the bottom or other portion of the cast, boot, shoe, mat, sock, insole, or lower extremity immobilization or protective device in a setting where such pressure could be deleterious or harmful (including situations where patients are recovering from a bony fracture, tendon injury, and recent lower extremity surgery).

17 Claims, 1 Drawing Sheet

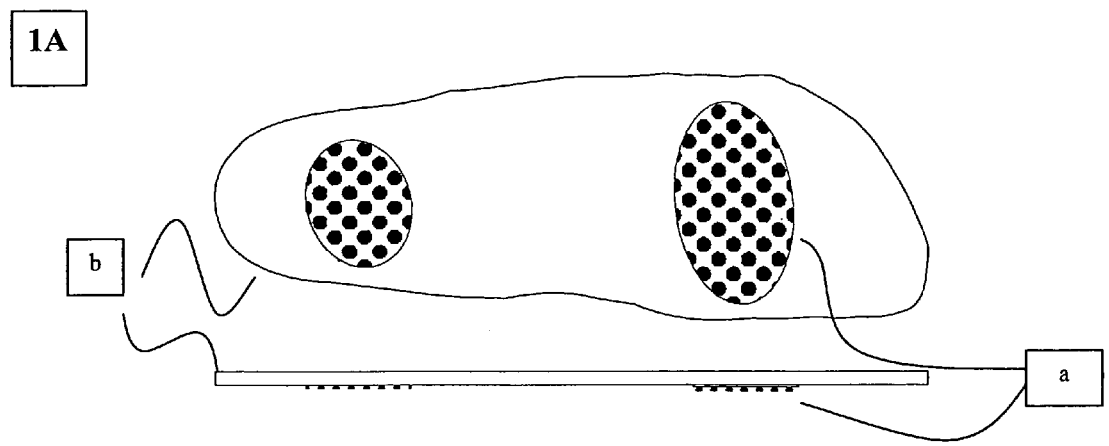
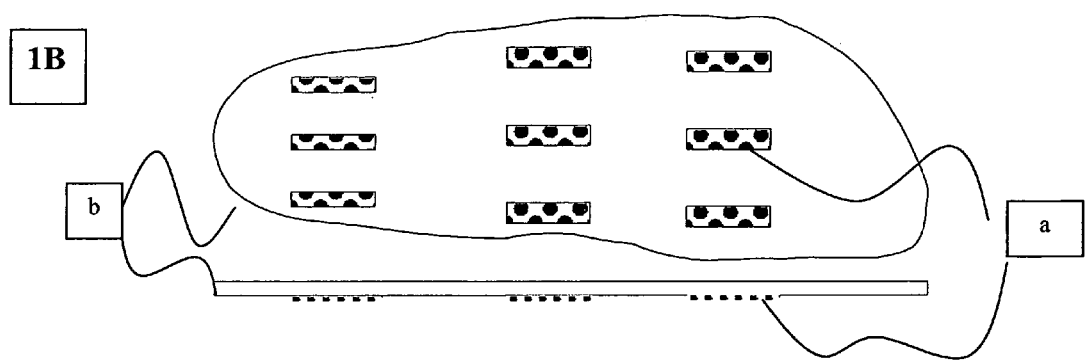
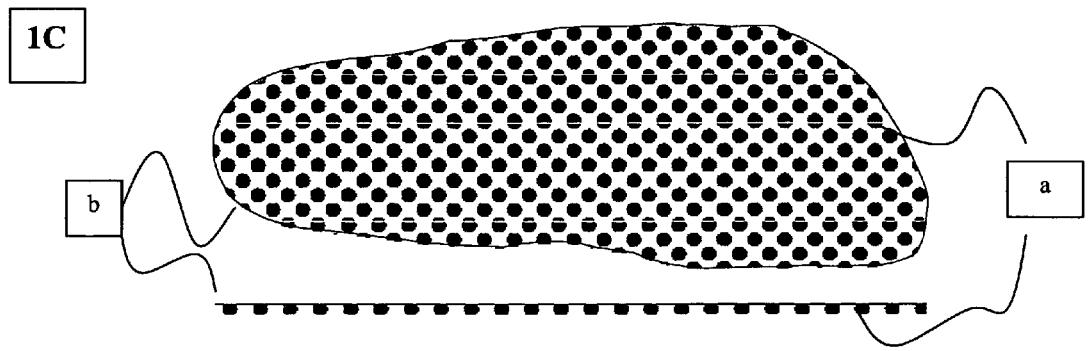

FOOT PRESSURE DETECTION DEVICE

BACKGROUND OF THE INVENTION

The current invention generally relates to an apparatus for detecting force or pressure applied to the bottom of a foot and lower extremity, and more particularly, to an apparatus for detecting the application of a predetermined threshold amount of force or pressure applied to a cast, boot, shoe, mat, insole, sock, or other lower extremity immobilization or protective device, where the predetermined threshold relates to a pressure threshold that could be deleterious or harmful if exceeded (including situations where patients are recovering from a bony fracture, tendon injury, and recent lower extremity surgery).

A recurring problem with recovery from an injury in a lower extremity, such as a leg or foot, is the risk of secondary injuries or trauma. As patients begin recovering, they naturally want to resume their typical routine, and in many cases the increased activity is part of their rehabilitation regime. However, even if a patient is generally aware and exercising care not to place undue pressure on a recovering extremity, it is difficult for most people to remember how much a given threshold weight feels like when using their legs, and even the best of patients find it difficult to remain conscious of the need to avoid more than that threshold, avoid missteps or loss of balance, or the like, all events which could lead to too much pressure being exerted.

To minimize the risk of new injury or trauma, a variety of alert devices have been developed to assist in warning patients as too much weight is being exerted. Despite the extensive development of such devices, they continue to exhibit certain disadvantages. For example, their designs are: (1) too complex, (2) too costly, (3) and fail to fully record and document all incidents in which too much pressure has been exerted. Thus, there exists a continuing need for the development of new and improved, easier to use and inexpensive devices for the detection of force or pressure applied to a cast, boot, shoe, mat, sock, insole, or other lower extremity immobilization or protective device.

SUMMARY OF THE INVENTION

Recognizing the need for the development of improved pressure monitoring under or within, for example, a cast, boot, shoe, mat, sock, insole or other lower extremity immobilization or protective device, the present invention is generally directed to satisfying the needs set forth above and overcoming these and other disadvantages with prior art devices and to providing a device that is comfortable or at least not uncomfortable when used.

An illustrative, but not inclusive, listing of advantages that may now be realized in various exemplary embodiments of the present invention include: providing a pressure detection device that is simple to construct and use and whose manufacturing costs my be kept to a minimum; providing a pressure detection device that will detect that a threshold of pressure has been applied to the bottom of a cast, boot, shoe, or other lower extremity immobilization or protective device; and providing a pressure detection device that will alert both the patient and health care provider detect that pressure has been applied to the bottom of a cast, boot, shoe, or other lower extremity immobilization or protective device, such that, for instance: (1) appropriate counseling may be undertaken, (2) further instruction or physical therapy can be provided to the patient, or (3) the protective device may be appropriately augmented.

BRIEF DESCRIPTION OF THE DRAWINGS

FIG. 1A diagrammatically illustrates a bottom and side view of a first exemplary embodiment of the present invention.

FIG. 1B diagrammatically illustrates a bottom and side view of a second exemplary embodiment of the present invention.

FIG. 1C diagrammatically illustrates a bottom and side view of a third exemplary embodiment of the present invention.

DESCRIPTION OF THE PREFERRED EMBODIMENTS

In the following, FIGS. 1A-1C diagrammatically illustrate various embodiments of the present invention. These figures respectively depict illustrative bottom and right side cross-sectional views each of different passive foot pressure detection devices in accordance with embodiments of the present invention. In this and the other figures, the symbol "•" is used to schematically represent pressure sensitive chambers.

In accordance with embodiments of the present invention, the pressure sensitive chambers are preferably designed to burst or otherwise release their contents at a known, e.g., pre-determined force or weight. As will be recognized by those skilled in the art, the pressure that the chambers burst depends upon the material of chambers and, for example, the thickness of the chamber walls. These parameters are well known to those skilled in the art, and are therefore not discussed herein.

The pressure sensitive chambers may be filled with air or other gases, a suitable liquid, or semi-liquid or releasable solids (e.g., a fine granular solid) material; either dyed or undyed. They can be filled with miniature or sub microscopic particulate transmitters that permit continuous or immediate identification of their location in space.

The pressure sensitive chambers themselves may be made from any appropriate material, such as plastics, and will typically be the same as the material of the base. The base material may be of any desired shape and thickness, e.g., up to several mm if serving as an insert. Or, for example, the base material need be no thicker than needed to serve as an adhesive tape. In the adhesive example, the adhesive can be on one side and the pressure sensitive chambers (e.g., micro-bubbles) formed onto the opposite side. The adhesive or attaching materials, when used, could be any suitable adhesive for attachment to a lower extremity device, such as a cast, a boot, a shoe, or other lower extremity immobilization or protective device ("LED"). The pressure sensitive device can be fabricated of any suitable material, such as, for example, plastic, polymer, cloth, foam, cork, rubber, natural or synthetic material, or some combination thereof of these materials. In some embodiment it may be desirable to select a material for the pressure sensitive chambers that is temperature and/or moisture resistant so that the pressure sensitive chambers do not spontaneous rupture prior to application of the predetermined force or pressure and so that the mechanical properties of the device are not altered upon exposure to the environment. The base can be constructed of the same material if desired.

While the present embodiments are preferably formed for lower extremity devices, the present invention is not limited to such use, and can be utilized in any manner where excessive force is desired to be monitored in connection with any limb, appendage or body part that when in contact with the environment creates a mechanical pressure.

In the exemplary embodiments, the device is preferably flat and may or may not have adhesive or some other method for securing the device such as, but not limited too, clasps, Velcro, etc, on the side opposite of the pressure sensitive chambers. Other ways of attaching the device may be used, such as adhesive tabs. Or course, in some situations, it is not necessary to secure the device.

In the exemplary embodiments, the shape of the device approximates the shape of the human foot in the transverse plane. However, the device may also be made in other shapes, including, but not limited to, oval, rectangular, circular, square, and eccentric shapes, or any limb, appendage or body part that when in contact with the environment creates a mechanical pressure desired to be monitored.

Referring to FIG. 1A, this figure diagrammatically illustrates a bottom and side view of a first exemplary embodiment of the present invention. In FIG. 1, there are two regions/clusters of pressure sensitive chambers (a); one located in the heel region of the base (b) and the other in the forefoot region of the base (b). In this case, a single pressure detection device ("PDD") can serve as an insert, e.g., formed to fit in shoes or other LED's without sliding, or as an externally attachable unit.

FIG. 1B diagrammatically illustrates a bottom and side view of a second exemplary embodiment of the present invention. In FIG. 1B, there are several regions/clusters of pressure sensitive chambers (a) distributed over the base (b) of the pressure detection device. The distribution of the pressure sensitive chambers (a) need not be uniform as shown in the example of FIG. 1B.

FIG. 1C diagrammatically illustrates a bottom and side view of a third exemplary embodiment of the present invention. In FIG. 1C, the pressure sensitive chambers (a) are distributed in a non-clustered fashion over the entire base (b) of the pressure sensitive device. Again, as in the exemplary embodiment of FIG. 1B, the distribution of the pressure sensitive chambers need not be uniform as shown in FIG. 1C.

In accordance with embodiments of the present invention, the pressure sensitive chambers can be arranged in rows and/or columns such that a set amount of force or pressure will burst substantially all the pressure sensitive chambers of one row, column, or cluster.

In accordance with one preferred embodiment of the present invention, a pressure detection device can be applied to the bottom of a cast, boot, shoe, or other lower extremity immobilization or protective device by, for example, an adhesive applied to the superior aspect of the PDD. The PDD comprises a single pressure sensitive chamber or set of pressure sensitive chambers, fixedly attached to a backing material or base, and with the adhesive on a first side of the material. When the adhesive is exposed or activated, a user (e.g., a medical doctor) applies the PDD to a desired region of the LED for monitoring pressure in that region. Multiple PDDs can be applied to different regions of the LED, allowing detection of excess pressure at each of the regions.

Further, the cell(s) of each PDD have a predetermined pressure threshold, which if exceeded leads to a destructive (e.g., bursting) or non-destructive (e.g., release via a valve, that can be refilled) change in the cell(s), which readily indicates that the threshold pressure was exceeded. A destructive release is preferred, as being the easiest and most economical form of PDD to make and maintain. If the PDDs are formed in the shape of strips (e.g., FIG. 2), all pressure sensitive chambers in a given strip can be conveniently designed to burst at the same pressure threshold, and different strips having different pressure thresholds can be designated by any convenient manner (e.g., color or alphanumeric coding on the strip). Alternatively, a given strip can be utilized that has pressure sensitive chambers with multiple thresholds. For example, a first threshold can be used to warn the patient visibly or by giving a popping noise, that he/she is using pressure close to an unsafe threshold, and pressure sensitive chambers with a second threshold can be used that burst when an unsafe threshold is exceeded. As will be recognized by those skilled in the art, the present invention contemplates that the pressure sensitive chambers be in the base, such as with material that has the chambers formed in the base such as, for example a suitably strengthened form of bubble wrap, to provide the popping, or on the base such as shown in the figures. The present invention is not limited to any particular structure or arrangement of the pressure sensitive chambers.

In another embodiment of the present invention, the pressure detection device may be inserted within some portion a cast, boot, shoe, mat, sock, insole, or other lower extremity immobilization or protective device.

In another embodiment of the present invention, the pressure detection device may be encased in a protective envelope consisting of a material that will protect the individual chambers from abrasive wear.

Alternatively, in another embodiment of the present invention, the pressure detection device may be covered with or positioned adjacent to an absorbent material or adsorbent material. Such materials can be selected, as known to those skilled in the art, to exhibit the efflux of the contents of the burst pressure sensitive chamber or chambers.

Of course, one skilled in the art will appreciate how a variety of alternatives are possible for the individual elements, and their arrangement, described above, while still falling within the spirit of the invention. Thus, for example, the pressure sensitive chambers may be any commercially available bursting cell. Examples of suitable base materials have been given above, and one skilled in the art will appreciate that a variety of different PDD(s) may be used with different LEDs, the particular selection being a matter of design choice. Any convenient material (adhesives, tapes, velcro patches, heat sealing, etc.) or process may be used to help fix the position of the pressure sensitive chambers of the PDD so they are maintained proximate the desired region of the LED/foot when worn. Alternatively, part of the attachment mechanism for the PDD/pressure sensitive chambers (e.g., the base of a 2-part velcro-style patch) can be formed as an part of a regular or specialized LED or LED insert if desired, already appropriately positioned when forming the LED.

While the above describes several embodiments of the invention used primarily in connection with an adjustable cell system in treating positional hindfoot disorder, those skilled in the art will appreciate that there are a number of alternatives, based on system design choices and choice of protocol options, and extensions that still fall within the spirit of my invention. Thus, it is to be understood that the invention is not limited to the embodiments described above, and that in light of the present disclosure, various other embodiments and applications should be apparent to persons skilled in the art. Accordingly, it is intended that the invention not be limited to the specific illustrative embodiments.

What is claimed is:

1. A passive pressure monitoring device comprising:
   an insert device for insertion into an immobilization device and for use in conjunction with monitoring pressure exhibited on a portion of a body, comprising:
      a base portion; and
      a plurality of pressure sensitive chambers arranged on the base in a predetermined pattern wherein the pattern is selected to detect a given pressure exhibited by a desired portion of a body in pressure contact with certain of the chambers, the certain of the pressure sensitive chambers having a predetermined threshold bursting strength selected so that the certain of the pressure sensitive chambers burst at the given pressure.

2. A monitoring device according to claim 1, wherein the base comprises at least one of: plastic, polymer, cloth, foam, cork, rubber, a natural material and a synthetic material.

3. A monitoring device according to claim 1, wherein the pressure sensitive chambers are filled with air.

4. A monitoring device according to claim 1, wherein the pressure sensitive chambers are filled with liquid.

5. A monitoring device according to claim 1, wherein the pressure sensitive chambers are filled with a semi-liquid material.

6. A monitoring device according to claim 1, wherein the pressure sensitive chambers are filled with a particulate material.

7. A monitoring device according to claim 6, wherein the pressure sensitive chambers are filled with miniature or sub microscopic particulate transmitters that permit continuous or immediate identification of their location in space.

8. A monitoring device according to claim 1, further comprising a protective envelope position to protect the individual pressure sensitive chambers from abrasive wear.

9. A monitoring device according to claim 1, further comprising an absorbent or adsorbent material positioned adjacent to the pressure sensitive chambers so that the material will exhibit the efflux of the contents of the burst chamber or pressure sensitive chambers.

10. A monitoring device according to claim 1, wherein the pressure sensitive chambers are arranged in clusters.

11. A monitoring device according to claim 1, wherein the pressure sensitive chambers are arranged in rows and columns such tat a set amount of force or pressure will burst substantially all the pressure sensitive chambers of one row, column, or cluster.

12. A monitoring device according to claim 1, wherein the device is structured so tat it is generally shaped when in contact with one of and in accordance to the shape of one of: a sole of a human foot, other limb, and a body part.

13. A monitoring device according to claim 1, where the device is of uniform or varying thickness to better conform to the portion of the body.

14. A monitoring device according to claim 1, further comprising:
at least one of a permanent and a non-permanent adhesive in operable contact with the base.

15. A monitoring device according to claim 1, wherein the pressure sensitive chambers comprise a material that is temperature and moisture resistant.

16. A passive pressure monitoring device comprising:
an attachable device for attachment to an immobilization device and for use in conjunction with monitoring pressure exhibited on a portion of a body, comprising:
a base portion;
a securing device for securing the base portion to the immobilization device; and
a plurality of pressure sensitive chambers arranged on the base in a predetermined pattern wherein the pattern is selected to detect a given pressure exhibited by a desired portion of a body in pressure contact with certain of the chambers, the certain of the pressure sensitive chambers having a predetermined threshold bursting strength selected so that the certain of the pressure sensitive chambers burst at the given pressure.

17. A passive pressure monitoring device according to claim 16, wherein the securing device includes at least one of: adhesive, a clap, a swap, a hook and loop fastener, tape, and a heat seal.

* * * * *